United States Patent [19]

Jamshidi

[11] 4,022,191
[45] May 10, 1977

[54] BIOPSY NEEDLE GUARD AND GUIDE

[76] Inventor: Khosrow Jamshidi, 610 Winston Court, St. Paul, Minn. 55118

[22] Filed: June 4, 1976

[21] Appl. No.: 692,632

[52] U.S. Cl. .................. 128/2 B; 128/215; 128/221

[51] Int. Cl.² .............................. A61B 5/00

[58] Field of Search ....... 128/2 B, 215, 216, 218 R, 128/218 N, 221, 239, 224, 348; 408/241 S

[56] References Cited

UNITED STATES PATENTS

| | | | |
|---|---|---|---|
| 1,465,851 | 8/1923 | Kress | 128/221 |
| 3,073,306 | 1/1963 | Linder | 128/215 |
| 3,073,307 | 1/1963 | Stevens | 128/221 |
| 3,094,124 | 6/1963 | Birtwell | 128/348 |
| 3,523,530 | 8/1970 | Pagones et al. | 128/221 X |

FOREIGN PATENTS OR APPLICATIONS

| | | | |
|---|---|---|---|
| 790,935 | 11/1935 | France | 128/221 |
| 651,436 | 4/1936 | Germany | 128/221 |

*Primary Examiner*—John D. Yasko
*Attorney, Agent, or Firm*—Orrin M. Haugen

[57] ABSTRACT

A biopsy specimen gathering system has been developed which includes a biopsy needle having an aspirating chamber operatively coupled thereto. An elongated tubular sleeve forming a sleeve guard is provided, the sleeve guard having a closed base and an open top with the inner periphery of the upper end of the sleeve having a surface for sealingly engaging the outer periphery of the base of the aspirating chamber. The outer circumference of the shank of the sleeve guard has a plurality of spaced-apart circumferential grooves formed therein to provide spaced score grooves to a depth sufficient to permit the shank to be broken upon flexure thereof, thereby leaving an open ended sleeve firmly attached to the aspirating chamber and exposing a desired length of the tubular needle.

5 Claims, 6 Drawing Figures

U.S. Patent  May 10, 1977  4,022,191
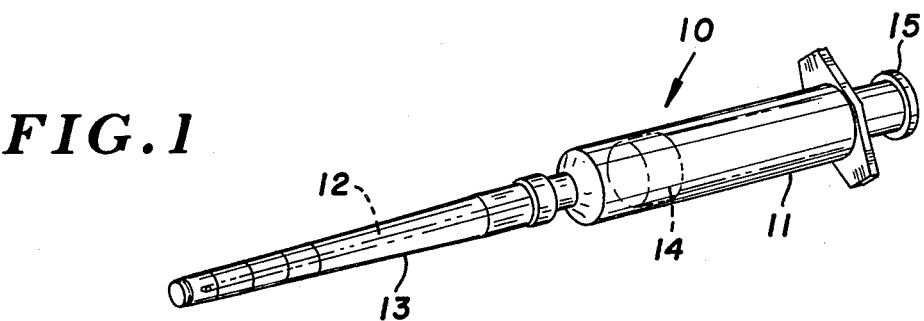
FIG.1
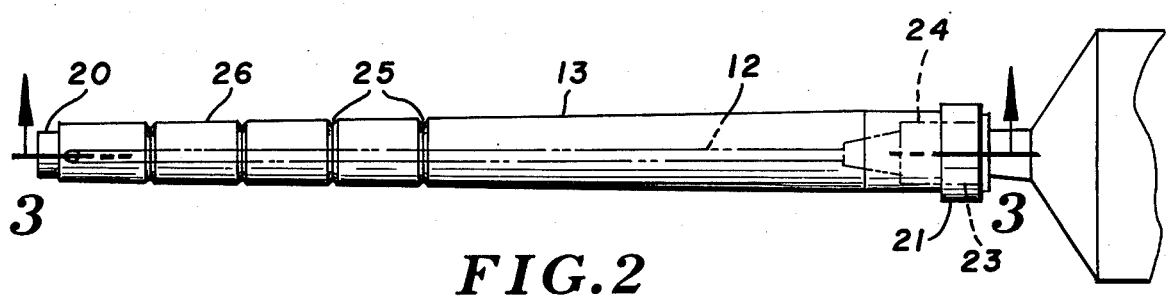
FIG.2
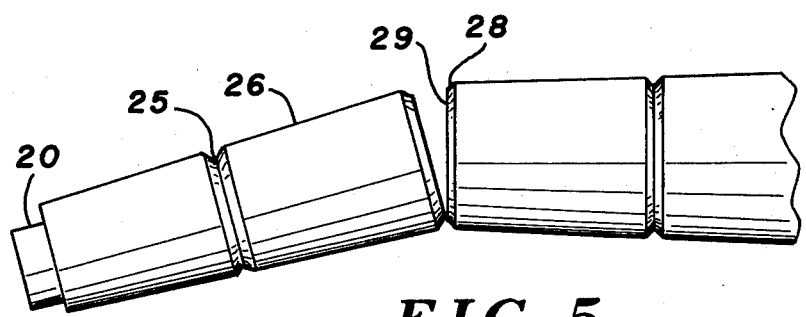
FIG.3
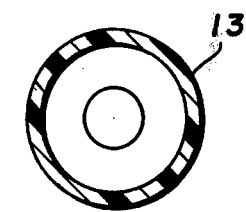
FIG.4
FIG.5
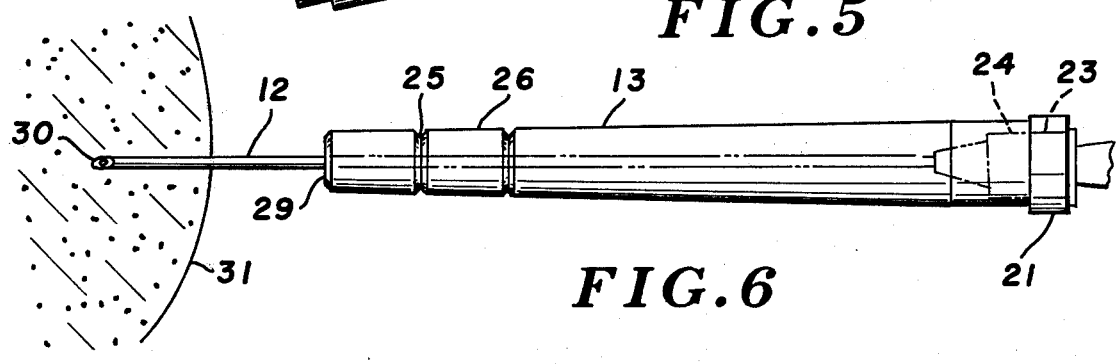
FIG.6

BIOPSY NEEDLE GUARD AND GUIDE

BACKGROUND OF THE INVENTION

The present invention relates generally to a biopsy collecting system, and more specifically to a biopsy collecting needle and guard assembly.

In the biopsy field, needles are frequently employed to gather or otherwise collect specimens for laboratory examination. The surgical procedure frequently requires that the surgeon be fully aware of the depth of penetration of the needle in order that a proper specimen be obtained. Since the outer surface of the biopsy specimen collecting needle is preferably smooth and polished, it is difficult to employ spaced markings along the surface of the needle so as to indicate depth of penetration of the tip. In accordance with the present invention, a sleeve guard has been designed which performs a dual function, the first being a sealing of the needle portion of the structure from the ambient, the second being the utilization of the guard as an indicator of the depth of penetration of the needle.

The biopsy specimen collecting needle is conventional, and may be, for example, designed in accordance with that certain claimed in U.S. Pat. No. 3,938,505 or, as an alternative that certain biopsy specimen collecting device disclosed and claimed in U.S. Pat. No. 3,882,849. In addition, a substantial number of other devices of this type are commercially available.

The sleeve guard element is fabricated from a frangible brittle material which, upon being scored, can be broken upon flexure. Therefore, in actual operation, the sleeve guard is placed over the tubular needle, with the upper end of the sleeve guard being arranged in sealing engagement with the outer periphery of the aspirating chamber, and specifically about the outer periphery of the needle hub. The outer circumference of the shank of the sleeve guard has a plurality of spaced apart circumferential grooves formed therein and disposed at spaced intervals along the length of the guard shank. These spaced score grooves are formed to a depth sufficient to permit the shank to be broken upon flexure so as to form an open ended sleeve exposing a predetermined portion of the tubular needle. The end surface of the broken guard therefore forms a base which functions as a stop for the needle upon entering the body of the patient from which the specimen is being obtained. Therefore, prior to use the guard forms a sealed enclosure for the needle, and subsequently, upon being broken in preparation for use of the specimen collecting system, the guard is broken off to the predetermined depth, thereby exposing the desired length of tubular needle required to perform the specimen collecting operation.

SUMMARY OF THE INVENTION

Therefore, it is a primary object of the present invention to provide an improved biopsy specimen collecting system which includes a needle having a guard disposed thereover, the guard functioning as a sealing enclosure prior to use, and being capable of controlled breaking in order to form a stop which exposes a predetermined length of needle shank for use.

It is a further object of the present invention to provide an improved biopsy specimen collecting needle system which includes a conventional specimen collecting system with an aspirating chamber and a needle extending therefrom, with a sleeve guard being provided to enclose and sealingly envelope the needle prior to use, and the guard being provided with spaced apart circular grooves to permit breaking or separation of the guard upon flexure thereof to form an open ended sleeve-stop exposing a predetermined length of tubular needle.

Other and further objects of the present invention will become apparent to those skilled in the art upon a study of the following specification, appended claims, and accompanying drawing.

BRIEF DESCRIPTION OF THE DRAWING

FIG. 1 is a perspective view of a biopsy specimen collecting system prepared in accordance with the present invention, and illustrating the sleeve guard arranged about the periphery of the needle portion of the specimen collecting system;

FIG. 2 is a side elevational view, on a slightly enlarged scale, of the needle portion of the system enclosed within the sleeve guard, and with a portion of the aspirating chamber being cut away;

FIG. 3 is a sectional view of the sleeve guard only of FIG. 2, with FIG. 3 being taken along the line and in the direction of the arrows 3—3 of FIG. 2;

FIG. 4 is a vertical sectional view of the sleeve guard portion and confined needle, with FIG. 4 being taken along the line and in the direction of arrows 4—4 of FIG. 3;

FIG. 5 is a detail side elevational view of the end portion only of the sleeve guard, with this figure being on a still larger scale, and illustrating the breaking or separation of the closed base and a portion of the length of the guard from the remainder of the guard; and FIG. 6 is a detail elevational view of the sleeve guard and needle assembly following the separation operation illustrated in FIG. 5, and illustrating the exposed needle portion entering the body of a patient.

DESCRIPTION OF THE PREFERRED EMBODIMENT

In accordance with the present invention, and particularly as illustrated in FIG. 1, the biopsy specimen collecting system generally designated 10 includes an aspirating barrel member 11 having a sample receiving hollow tubular needle 12 extending therefrom, needle 12 being enclosed within sleeve guard 13. The system further includes a conventional plunger and handle assembly with the plunger being illustrated at 14, and with the handle being illustrated at 15. The needle and aspirating portions of the device are, of course, commercially available. As has been indicated, the sleeve guard 13 provides a means by which the needle may be substantially sealingly enclosed prior to use, and immediately preparatory to use, the guard may be flexed and broken at a desired point along the length thereof so as to expose a predetermined or desired portion of the needle, with the edge of the sleeve portion remaining on the needle forming a stop to limit further movement of the needle within the body of the patient. By this fashion, therefore, biopsy techniques are simplified and the surgeon is always aware of the location of the needle tip while he is performing the biopsy specimen collecting operation.

With attention now being directed to FIGS. 2–5 of the drawing, the sleeve guard 13 includes an elongated tubular sleeve having a closed base at 20, and an open top as at 21. The inner periphery of the upper end of the tubular as at 22 is arranged to have sealing engagement with the outer surface 23 of needle hub 24, thus providing a protective environment for needle 12 while retained within the confines of sleeve guard 13. Sleeve guard 13 may be fabricated from any of a variety of materials, including, for example, polyethylene, polypropylene, polytetrafluoroethylene, polystyrene, or the like. It is preferred that the material of construction be somewhat brittle or frangible in order to enhance the breaking operation as is illustrated in FIG. 5. Such material is, of course, commercially available. Generally speaking, molded polystyrene is preferred because of its frangible characteristics.

Generally, a wall thickness of approximately 3mm-5mm may be emloyed, with the circumferential grooves, as illustrated at 25—25 being formed to a depth of approximately ½ of the total wall thickness.

The circumferential grooves 25—25 permit and enhance breaking of the shank upon flexure thereof. In this connection, the shank portion 26 of sleeve guard 13 may be broken upon flexing the member about the circumferential groove 28 as illustrated in FIG. 5. Flexure accordingly encourages rupture, fracturing, or breaking of the sleeve, where indicated, leaving a relatively smooth angular surface as at 29 to function as a stop or depth of penetration indicator for the needle 12.

With attention now being directed to FIG. 6, it will be seen that during the biopsy specimen collecting operation, the distal tip end 30 of needle 12 which is sharpened, as indicated, penetrates the body 31 of the patient to a depth which is controllably predetermined by the sleeve guide forming the stop area as at 29. The surgeon can readily determine the extent to which the needle has penetrated the patient, and thereby is informed at all times of the location of the tip 30. In view of the manner in which the inner periphery 22 of the upper end of the tubular sleeve forming the sleeve guard mates or grips with the outer surface of the needle hub, as at 23, the inner surface of the sleeve guard is normally spaced outwardly from the outer surface of the needle, thereby forming an annulus therebetween. This arrangement enhances the stopping and guiding features of the guard, since operation in any orientation is possible without risk of drop, separation, or loss of the sleeve guard during the biopsy procedure.

It will be appreciated that the combination of the present invention may be fabricated in a variety of sizes and configurations, the precise size and configuration being determined primarily by the application indicated for the specimen collecting system. For example, the arrangement is particularly adapted for use in connection with the collecting of biopsy specimens from internal organs such as liver, spleen, kidney, or the like, where the organ is disposed at a predetermined distance from the skin surface of the patient. In other applications, specific locations may be indicated for exploration, and the device may be tailored to any such use.

I claim:

1. In combination with a biopsy specimen collecting needle having an aspirating chamber and a tubular needle coupled thereto at the proximal end of the needle, the needle having a sharpened tip at the distal end and an aspirating chamber receiving hub at the proximal end thereof, and having a shank with a bore extending therethrough disposed therebetween; and sleeve guard means coupled to said tubular needle along said hub, with the guard enclosing and encapsulating said tubular needle therewithin; said sleeve comprising:
  a. an elongated tubular sleeve having a closed base and an open top, with the inner periphery of the upper end of said tubular sleeve having a surface for sealingly engaging the outer periphery of said needle hub; and
  b. the outer circumference of the shank of said sleeve guard having a plurality of spaced apart circumferential grooves formed therein and disposed along that portion of the length of said sleeve guard shank enclosing said tubular needle, said circular grooves forming spaced apart score lines of a depth sufficient to permit said sleeve shank to be broken along said score lines upon flexure thereof to form an open ended sleeve exposing a predetermined portion of said tubular needle.

2. The combination as defined in claim 1 being particularly characterized in that said tubular sleeve is fabricated from polystyrene.

3. The combination as defined in claim 1 being particularly characterized in that the inner diameter of said sleeve guard is spaced outwardly from the outer diameter of said tubular needle so as to define an annular chamber therebetween.

4. The combination as defined in claim 1 being particularly characterized in that the inner periphery of the upper end of said tubular sleeve grippingly engages the outer peripheral surface of said needle hub.

5. The combination as defined in claim 1 being particularly characterized in that said circular grooves extend substantially through the cross-sectional wall thickness of said sleeve guard to leave a relatively thin annular cross-sectional portion intact.

* * * * *